United States Patent [19]

Acheson et al.

[11] 4,122,272
[45] Oct. 24, 1978

[54] QUATERNARY 6,7-DIHYDRO-[5H]-THIAZOLO[3,2-A]PYRIMIDINIUM SALTS

[75] Inventors: Richard M. Acheson, Oxford; Ian R. Cox, North Harrow; John K. Stubbs; Alexander B. Penrose, both of Deal, all of England

[73] Assignee: Pfizer Inc., New York, N.Y.

[21] Appl. No.: 812,171

[22] Filed: Jul. 1, 1977

Related U.S. Application Data

[62] Division of Ser. No. 738,382, Nov. 2, 1976, Pat. No. 4,076,817.

[30] Foreign Application Priority Data

Nov. 5, 1975 [GB] United Kingdom ............... 45961/75
Nov. 5, 1975 [GB] United Kingdom ............... 45962/75

[51] Int. Cl.² .......................................... C07D 513/04
[52] U.S. Cl. .................................... 544/278; 544/250
[58] Field of Search ................. 260/251 A, 256.4 F; 424/251

[56] References Cited

PUBLICATIONS

Ried et al, Chemical Abstracts, vol. 82, 155,120f (1975).
Dhaka et al, Chemical Abstracts, vol. 79, 137,110m (1973).

Primary Examiner—Donald G. Daus
Assistant Examiner—Diana G. Rivers
Attorney, Agent, or Firm—Connolly and Hutz

[57] ABSTRACT

Quaternary 5,6-dihydroimidazo[2,1-b]thiazolium salts and novel quaternary 6,7-dihydro-[5H]thiazolo[3,2-a]pyrimidinium and 5,6,7,8-tetrahydrothiazolo[3,2-a][1,3]diazepinium salts, their preparation and preferred use as acaricidal agents are disclosed.

8 Claims, No Drawings

QUATERNARY 6,7-DIHYDRO-[5H]-THIAZOLO[3,2-A]PYRIMIDINIUM SALTS

CROSS-REFERENCE TO RELATED APPLICATION

This application is a division of application Ser. No. 738,382, filed Nov. 2, 1976, now U.S. Pat. No. 4,076,817.

BACKGROUND OF THE INVENTION

1. Field of the Invention

The invention relates to novel 8-substituted-6,7-dihydro[5H]thiazolo[3,2-a]pyrimidinium and 9-substituted-5,6,7,8-tetrahydrothiazolo[3,2-a][1,3]diazepinium salts and 7-substituted-5,6-dihydroimidazo[2,1-b]thiazolium salts. The latter series of compounds have been generically disclosed as hypoglycemic agents and growth promotants in U.S. Pat. No. 3,954,784. It has now been found that all of the above salts are useful acaricidal agents and are particularly effective in destroying ticks and mites which tend to infect the skins of animals, especially sheep and cattle, and are therefore useful as ectoparasiticidal agents for treating such animals.

2. Description of the Prior Art

All stages in the life cycle of the tick tend to damage the skins of afflicted animals and thereby spoil the state of the skins, with the consequence for example, that cattle hides and sheep skins intended for manufacture of leather and sheep skin respectively, are reduced in quality. Furthermore, the ticks may facilitate the transmission of disease to the afflicted animal, and the general state of health and the quality of flesh of the animal may be detrimentally affected.

U.S. Pat. No. 3,954,784 discloses quaternary 7-substituted imidazo[2,1-b]thiazolium salts of the formula:

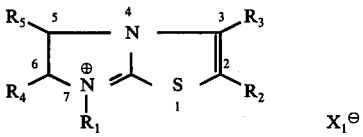

wherein $X_1^\ominus$ is a pharmaceutically acceptable anion, preferably chloride or bromide ion; $R_1$ is alkyl having from 12 to 18 carbon atoms; $R_2$ is hydrogen or alkyl having from one to three carbon atoms; $R_3$ is $R_2$, phenyl or substituted phenyl wherein said substituent is dimethyl or dimethoxy; $R_2$ and $R_3$ taken together is tetramethylene and $R_4$ and $R_5$ may be hydrogen. The preparation and use of these compounds as hypoglycemic agents and growth promotants is also disclosed therein.

SUMMARY OF THE INVENTION

It is an object of the invention to provide a series of compounds having acaricidal properties, particularly against cattle ticks, pharmaceutical compositions comprising such compounds and a method for protecting animals from acarids by treating said animals with said compounds.

The invention therefore provides novel 8-substituted-6,7-dihydro[5H]thiazolo[3,2-a]pyrimidinium and 9-substituted-5,6,7,8-tetrahydrothiazolo[3,2-a][1,3]diazepinium salts of the formula (I):

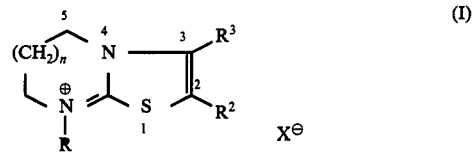

wherein $X^\ominus$ is a pharmaceutically acceptable anion; $R^1$ is an alkyl group having from 10 to 20 carbon atoms; $n$ is 1 or 2; each of $R^2$ and $R^3$ is selected from the group consisting of hydrogen, alkyl having from one to six carbon atoms, phenyl and phenyl substituted by up to two members which may be the same or different and are selected from the group consisting of fluoro, chloro, bromo, hydroxyl, alkyl having from one to three carbon atoms, alkoxy having from one to three carbon atoms, cyano, nitro, and trifluoromethyl; and $R^2$ and $R^3$ taken together form a tetramethylene group.

It is preferred that $X^\ominus$ is chloride, bromide or iodide ion and bromide ion is especially preferred.

A preferred group of compounds are those wherein $R^1$ is alkyl having from 10 to 18 and especially 15 to 17 carbon atoms; $R^2$ is hydrogen or methyl and $R^3$ is methyl, ethyl or phenyl.

The invention also provides an acaricidal composition comprising a diluent or carrier and an acaricidally effective amount of a compound selected from those of the formulae (IV), (V) and (VI).

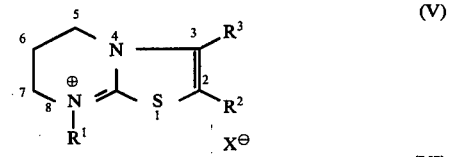

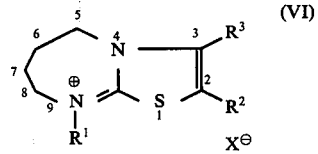

wherein $X^\ominus$ and $R^1$, $R^2$ and $R^3$ are as previously defined; with the proviso that in formula (IV) $R^2$ is other than hydrogen, phenyl and said substituted phenyl and $R^3$ is other than hydrogen.

The invention further provides a method for protecting animals from acarids which comprises externally treating said animals with an acaricidal amount of a compound of the formula (IV), (V) or (VI). Particularly effective in providing protection from acarids by this method are compounds of formula (IV) wherein $X^\ominus$ is bromide ion, $R^1$ is alkyl having from 10 to 18 carbon atoms, $R^2$ is methyl and $R^3$ is phenyl; compounds of formula (V) wherein $X^\ominus$ is bromide ion, $R^1$ is n-tetradecyl or n-hexadecyl, $R^2$ is methyl and $R^3$ is methyl or ethyl as well as compounds of formula (VI) wherein $X^\ominus$ is bromide ion, $R^1$ is n-pentadecyl or n-hexadecyl; $R^2$ is hydrogen or methyl and $R^3$ is methyl or phenyl.

Particularly preferred individual novel compounds of the invention include the following compounds wherein the $R^1$ substituent is a n-alkyl group;

8-tetradecyl- and 8-hexadecyl-substituted derivatives of 3-ethyl-2-methyl-6,7-dihydro-[5H]-thiazolo[3,2-a]pyrimidinium bromide; 8-hexadecyl-2-methyl-3-phenyl-6,7-dihydro-[5H]-thiazolo[3,2-a]pyrimidinium bromide; 8-pentadecyl-, 8-hexadecyl- and 8-heptadecyl-3-phenyl-6,7-dihydro-[5H]-thiazolo[3,2-a]pyrimidinium bromides; the 9-tetradecyl to 9-heptadecyl substituted derivatives of 3-methyl- and 3-phenyl-5,6,7,8-tetrahydrothiazolo[3,2-a][1,3]diazepinium bromide; 9-hexadecyl-2-methyl-3-phenyl-5,6,7,8-tetrahydro-thiazolo[3,2-a][1,3]diazepinium bromide; and 9-hexadecyl-2,3-tetramethylene-5,6,7,8-tetrahydrothiazolo[3,2-a][1,3]diazepinium bromide.

DETAILED DESCRIPTION OF THE INVENTION

In the formulae used herein, the quaternary nitrogen is arbitrarily shown in the 7-, 8- or 9-position, but is may also be in the 4-position, the double bond then being to that nitrogen. There also may be resonance between these two structures.

Methods for the preparation of compounds of formula (IV) are described in U.S. Pat. No. 3,954,784 and in the corresponding Belgian Pat. No. 820,186 published Mar. 20, 1975. The compounds of formulae (I), (V) and (VI) can be readily prepared in a similar manner from compounds of formula (II):

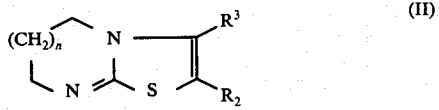
(II)

where $n$, $R^2$ and $R^3$ are as previously defined, by treatment with alkylating agents such as, for example, those of the formula $R^1$—halogen, where halogen is Cl, Br or I, sulphates of the formula $(R^1)_2SO_4$ or $R^1HSO_4$ or aryl sulphonates of the formula $R^1OSO_2Ar$, where Ar is an aryl group such as, for example, phenyl, tolyl or xylyl, to form a quaternary salt of formula (I) in which $X^\ominus$ is the corresponding anion, e.g., chloride, bromide, iodide, sulphate, hydrogen sulphate, benzene sulphonate or p-toluene sulphonate. Preferred values of $X^\ominus$ are the above mentioned halides, especially bromide. Such salts can be converted to other pharmaceutically acceptable salts, if desired, by conventional means, see, for example, U.S. Pat. No. 3,954,784. Examples of such other pharmaceutically acceptable anions are nitrate, phosphate, acid phosphate, acetate, fumarate, lactate, citrate, tartarate, gluconate, p-toluenesulphonate and pamoate.

Reaction with the alkylating agent may be conveniently carried out by dissolving or suspending the compound of formula (II) as free base in the alkylating agent either neat or in the presence of a suitable reaction inert solvent, i.e. a solvent which does not react to any appreciable degree with the reactants or product under the conditions of the reaction. Suitable reaction inert solvents can be of a varied nature, and can include lower alkanols such as methanol, butanol and isoamyl alcohol; lower alkylnitriles such as acetonitrile, propionitrile; di(lower)alkylketones such as acetone, diethyl ketone and methyl ethyl ketone; lower alkylethers such as ethyl ether, isopropyl ether and methyl butyl ether and N,N-dimethylformamide. Preferred solvents for this reaction are acetonitrile and N,N-dimethylformamide.

When the reaction is conducted neat, it is preferred that the alkylating agent employed is a liquid at the reaction temperature employed. The alkylating agent is preferably added at room temperature and the mixture reacted at a temperature from about room temperature up to the reflux temperature of the solvent, if present, for periods up to 24 hours. Typically, when acetonitrile is employed as solvent the reaction mixture is held at reflux for 16 hours.

On cooling the reaction mixture, if necessary to a temperature as low as $-10°$ C., the desired product will separate as solid which is filtered off and washed with a suitable non-solvent for the product, e.g. petroleum ether. Alternatively the solvent is removed by evaporation and the product washed as before. Recrystallization from a suitable solvent for the product e.g. ethereal acetonitrile will then normally yield the product in a pure state.

The compounds of formula (II) used as starting materials are either known compounds or can readily be prepared by methods analogous to those described in the literature, e.g. by reaction of a N,N-tri or tetramethylenethiourea of the formula:

(III)

where $n$ is 1 or 2, with an $\alpha$-halo-aldehyde or ketone of the formula $R^2CHZCOR^3$, where Z is Cl or Br. Thus the preparation of 6,7-dihydro[5H]thiazolo[3,2-a]pyrimidines is described by Chadha and Pujari in *Canadian J. Chem.*, 1969, 47, 2843, by Gakhar, Kaushal and Narang in *Indian J. Appl. Chem.*, 1970, 33, 269 and in West German Offenlegungsschrift No. 1,805,948 while the preparation of 5,6,7,8-tetrahydro-thiazolo[3,2-a][1,3]diazepines is described by Chadha, Chaudhary and Pujari in *Australian J. Chem.*, 1969, 22, 2697, by Dhaka, Chadha and Pujari in *Indian J. Chem.*, 1973, 11, 554 and in U.S. Pat. No. 3,763,142.

The above-mentioned $\alpha$-haloaldehydes and $\alpha$-haloketones are available either commercially or by synthetic procedures familiar to those skilled in the art.

The compounds of the formulae (I), (IV), (V) and (VI) have acaricidal activity, particularly against all stages in the life cycle, including gravid female ticks, of the cattle ticks *Boophilus microplus* and *Haemaphysalis longicornus*.

In one test, five freshly collected, fully engorged *Boophilus microplus* adult ticks are used for each acaricidal compound. Using a micro-pipette, 10 micro-liters of a solution containing 10 micro-grams of the acaricidal compound in ethanol or acetone, is applied to the dorsal surface of each of the ticks. The treated ticks are placed in weighed $1 \times 2$ inch glass vials, weighed and stored at 26° C. and 80% relative humidity in plastic boxes for 2 weeks. The ticks are then removed from the vials and the vials weighed to give the weight of eggs laid by the ticks. Any reduction in the egg laying of the treated ticks is caculated as a percentage of the eggs laid by untreated control ticks.

The eggs are returned to the incubator for a further 3 weeks after which time the percentage of eggs hatching is estimated.

The percentage effect is calculated as the overall reduction in the anticipated reproduction of the ticks using the weight of eggs laid and the percentage of eggs hatching.

The test may be repeated using smaller amounts of the acaricidal compound for sufficiently active compounds.

In another test, using a pipette 0.5 ml. of a solution containing 0.5 mg. of the acaricidal compound in ethanol or acetone is spread evenly on to a Whatman No. 1 filter paper 8 cm. × 6.25 cm. (50 sq. cm.) to give a dosage of 100 mg./m².

The treated paper is allowed to dry at room temperature, folded with the treated surface inside the two short edges sealed with a crimping machine. The open ended envelope is placed in a 1 lb. Kilner jar containing damp cotton wool in a plastic pot and stored in an incubator at 26° C. for 24 hours. 20–50 *Boophilus microplus* larvae, which had hatched 8–14 days previously, are placed in the envelope using a small spatula. The open end is then crimped to form a sealed packet. The treated paper containing the larvae is returned to the Kilner jar and kept for a further 48 hours in the incubator. 20–50 larvae are placed similarly in an untreated paper envelope to act as controls. At the end of the 48 hours test period, the mortality is noted and recorded as a percentage after correction for any mortality among the untreated control ticks.

The test may be repeated using smaller amounts of the acaricidal compound.

In addition to percentage effectiveness figures, $ED_{50}$ results can be obtained from dose response measurements using any of the aforedescribed tests.

Activity against *Haemaphysalis longicornus* nymphs may be measured in a similar manner to the above larvae test.

The activity of many of the compounds of the Examples detailed hereinafter against the tick *Boophilus microplus* has been determined. Table I shows the % effect for the compounds at the dose levels tested.

TABLE I

| | In Vitro Activity (topical application) vs. Adult Boophilus microplus % Effect | | | | | |
|---|---|---|---|---|---|---|
| | Dose µg/tick | | | | | |
| Example No. | 10 | 8 | 4 | 2 | 1 | 0.5 |
| 1 | 100 | 100 | 100 | 99 | 59 | 24 |
| 2 | 100 | 100 | 77 | 67 | 16 | |
| 3 | 100 | 97 | 90 | 26 | 13 | 2 |
| 4 | 83 | 100 | 75 | 12 | | |
| 5 | 65 | 63 | 32 | 4 | 0 | |
| 6 | 100 | 98 | 79 | 43 | 7 | |
| 7 | 100 | 100 | 99 | 92 | 54 | 31 |
| 8 | 26 | | | | | |
| 9 | 42 | | | | | |
| 10 | 72 | | | | | |
| 11 | 100 | 100 | 100 | 73 | 36 | 30 |
| 12 | 100 | 87 | 38 | 22 | 19 | 16 |
| 13 | 100 | 99.9 | 99.4 | 21 | 6 | 0 |
| 14 | 47 | | | | | |
| 15 | 100 | 100 | 99.9 | 29 | 9 | 11 |
| 16 | 33 | | | | | |
| 19 | 49 | 28 | 9 | 0 | | |
| 20 | 100 | 100 | 99 | 67 | 29 | 0 |
| 21 | 100 | 100 | 98 | 83 | 0 | |
| 22 | 57 | | | | | |
| 23 | 100 | 100 | 100 | 98 | 60 | 6 |
| 24 | 100 | 100 | 97 | 70 | 48 | 13 |
| 25 | 98 | 78 | 82 | 40 | 20 | |
| 26 | 99 | 92 | 61 | 43 | 12 | 14 |
| 27 | 86 | 75 | 63 | 55 | 38 | 40 |
| 28 | 100 | 83 | 74 | 52 | 13 | |
| 29 | 100 | 100 | 55 | 11 | 19 | |
| 30 | 100 | 95 | 56 | 47 | 13 | |
| 31 | 100 | 52 | 0 | | | |
| 32 | 100 | 95 | 94 | 66 | 19 | 0 |

TABLE I-continued

| | In Vitro Activity (topical application) vs. Adult Boophilus microplus % Effect | | | | | |
|---|---|---|---|---|---|---|
| | Dose µg/tick | | | | | |
| Example No. | 10 | 8 | 4 | 2 | 1 | 0.5 |
| 33 | 100 | 72 | 30 | 13 | 2 | 2 |
| 34 | 32 | | | | | |
| 35 | 100 | 100 | 70 | 13 | 8 | 0 |
| 36 | 26 | | | | | |
| 37 | 87 | | | | | |
| 38 | 30 | | | | | |
| 41 | 92 | 43 | 16 | 18 | 18 | 5 |
| 42 | 100 | 100 | 90 | 50 | 52 | 6 |
| 43 | 100 | 100 | 96 | 72 | 23 | 4 |
| 44 | 100 | 100 | 93 | 89 | 63 | 0 |
| 45 | 88 | | | | | |
| 46 | 95 | | | | | |

Thus the invention provides an acaricidal composition comprising an acaricidally effective amount of a compound selected from those of the formulae (IV), (V) and (VI) together with a diluent or carrier. The diluent or carrier may be a solid or a liquid, optionally together with a dispersing agent, emulsifying agent or wetting agent. The compositions of the invention include not only compositions in a suitable form for application but concentrated primary compositions which may be supplied to the user and which require dilution with a suitable quantity of water or other diluent prior to application. Typical compositions of the invention include, for example, dusting powders, dispersible powders, solutions, dispersions, emulsions and emulsifiable concentrations.

A dust may be made by mixing the appropriate amount of the finely divided active compound with a solid pulverulent diluent or carrier such as talc, clay, calcite, pyrophyllite, diatomaceous earth, walnut shell flour, silica gel, hydrated alumina, or calcium silicate. As an alternative method of preparation, the diluent or carrier is mixed with a solution of the active compound in a volatile organic solvent such as toluene, the solvent being subsequently removed by evaporation. Preferably, the active compound will be present in the dust in an amount of from about 0.25 to about 4% by weight.

Dispersible powders, of special value for spray applications, may be made by adding a suitable dispersing agent to the active compound, or to a dust containing the active compound, so that a stable aqueous dispersion of the active compound is formed on mixing the powder with water. The dispersible powders preferably contain from about 25 to 75% by weight of the active compound.

Emulsifiable concentrates comprise a solution of the active compound in a substantially water-immiscible non-toxic organic solvent containing an emulsifying agent. Suitable solvents include, for example, toluene, xylene, petroleum oil, and alkylated naphthalenes. Preferably, the concentrate will contain 5–75 gms. of the active compound per 100 ml. of solution. The concentrates may be diluted with water prior to use to give a concentration of the active compound in the aqueous medium of from e.g. about 0.0005 to about 0.1% w/v (g/100 ml.) or approximately 5 to 1000 p.p.m. The volatile solvents, e.g. toluene and xylene, evaporate after spraying to leave a deposit of the active ingredient. The made up spray or dip may be an emulsion or solution.

The compositions of the invention may be applied to ground, such as that around dairies, in order to combat, e.g. cattle ticks thereon. However, it is preferred to treat animals by spraying them or passing them through animal dips.

Thus the present invention also provides a method for protecting animals, particularly cattle, from acarids, particularly cattle ticks, which comprises treating the animal externally with an acaricidal amount of a compounds selected from those of the formulae (IV), (V) and (VI) or acaricidal composition as defined above.

EXAMPLES 2 TO 19

The following compounds were prepared by the general method described in Example 1 starting from the appropriately substituted 6,7-dihydro-thiazolo[3,2-a]pyrimidine and the appropriate alkyl bromide. Table 2 shows the compounds prepared together with the melting point and analytical data for each.

TABLE 2

| Example No. | $R^1$ | $R^2$ | $R^3$ | m.p. °C. | Analysis % (Theoretical in brackets) | | |
|---|---|---|---|---|---|---|---|
| 2 | —(CH$_2$)$_{14}$CH$_3$ | H | —C$_6$H$_5$ | 133–5° | C, 63.5 (C, 63.9 | H, 8.6 H, 8.5 | N, 5.3 N, 5.5) |
| 3 | —(CH$_2$)$_{15}$CH$_3$ | H | —C$_6$H$_5$ | 135–7° | C, 64.0 (C, 64.5 | H, 8.7 H, 8.7 | N, 5.2 N, 5.4) |
| 4 | —(CH$_2$)$_{13}$CH$_3$ | —CH$_3$ | —CH$_2$CH$_3$ | 60–62° | C, 59.6 (C, 60.1 | H, 9.8 H, 9.4 | N, 6.2 N, 6.1) |
| 5 | —(CH$_2$)$_{13}$CH$_3$ | H | —CH$_3$ | 86–88° | C, 58.1 (C, 58.5 | H, 9.2 H, 9.1 | N, 6.6 N, 6.5) |
| 6 | —(CH$_2$)$_{16}$CH$_3$ | H | —C$_6$H$_5$ | 139–141° | C, 65.2 (C, 65.0 | H, 8.8 H, 8.8 | N, 5.4 N, 5.2) |
| 7 | —(CH$_2$)$_{15}$CH$_3$ | —CH$_3$ | —C$_6$H$_5$ | 56–58° | C, 63.0 (C, 62.9 | H, 8.6 H, 8.9 | N, 5.0 N, 5.1)** |
| 8 | —(CH$_2$)$_{17}$CH$_3$ | H | —CH$_3$ | 117–119° | C, 60.3 (C, 60.5 | H, 10.0 H, 9.7 | N, 5.2 N, 5.6)* |
| 9 | —(CH$_2$)$_{16}$CH$_3$ | H | —CH$_3$ | 88–90° | C, 60.1 (C, 59.7 | H, 9.7 H, 9.6 | N, 5.9 N, 5.8)* |
| 10 | —(CH$_2$)$_{14}$CH$_3$ | H | —CH$_3$ | 104–106° | C, 58.0 (C, 58.1 | H, 9.1 H, 9.3 | N, 6.2 N, 6.2)* |
| 11 | —(CH$_2$)$_{14}$CH$_3$ | —CH$_3$ | —C$_6$H$_5$ | 61–63° | C, 64.2 (C, 64.5 | H, 8.2 H, 8.7 | N, 4.9 N, 5.4) |
| 12 | —(CH$_2$)$_{17}$CH$_3$ | —CH$_3$ | —C$_6$H$_5$ | 62–64° | C, 65.0 (C, 65.0 | H, 8.9 H, 9.2 | N, 4.7 N, 4.9)* |
| 13 | —(CH$_2$)$_{13}$CH$_3$ | —CH$_3$ | —C$_6$H$_5$ | 45–50° | C, 61.3 (C, 61.7 | H, 8.4 H, 8.6 | N, 5.25 N, 5.3)+ |
| 14 | —(CH$_2$)$_{17}$CH$_3$ | H | —C$_6$H$_5$ | 140–142° | C, 65.2 (C, 65.6 | H, 8.9 H, 9.0 | N, 4.8 N, 5.1) |
| 15 | —(CH$_2$)$_{16}$CH$_3$ | —CH$_3$ | —C$_6$H$_5$ | 61–62° | C, 63.5 (C, 63.5 | H, 9.0 H, 8.7 | N, 5.0 N, 4.9)+ |
| 16 | —(CH$_2$)$_{15}$CH$_3$ | —C$_6$H$_5$ | H | 139–140° | C, 64.4 (C, 64.5 | H, 8.6 H, 8.7 | N, 5.3 N, 5.4) |
| 17 | —(CH$_2$)$_{13}$CH$_3$ | H | —C$_6$H$_5$ | 131–133° | C, 63.2 (C, 63.3 | H, 8.4 H, 8.4 | N, 5.3 N, 5.7) |
| 18 | —(CH$_2$)$_{11}$CH$_3$ | H | —C$_6$H$_5$ | 119–121° | C, 61.9 (C, 61.9 | H, 8.0 H, 8.0 | N, 5.9 N, 6.0) |
| 19 | —(CH$_2$)$_{15}$CH$_3$ | H | —CH$_3$ | 116–117° | N, 6.0 (N, 6.2 | Br, 17.6 Br, 17.4) | |

+calculated for hydrate
*calculated for hemihydrate
**calculated for monohydrate The compositions of the invention may also contain a pesticide, fungicide, additional acaricide, or the like.

The invention is illustrated by the following Examples:

EXAMPLE 1

3-Ethyl-2-methyl-6,7-dihydro-[5H]-thiazolo[3,2-a]pyrimidine (1.8 g., 0.01 mole) (prepared by basification of the hydrobromide salt with sodium carbonate) and cetyl bromide (3.3 g., 0.011 mole) were refluxed in acetonitrile solution for 16 hours. The solvent was evaporated and the residual oil solidified by stirring under dry ether at 0° C. Recrystallization from a mixture of acetonitrile and ether gave 8-cetyl-3-ethyl-2-methyl-6,7-dihydro[5H]thiazolo[3,2-a]pyrimidinium bromide, (0.92 g., 20%), m.p. 63°–66° (Found: C, 61.4; H, 9.6; N, 5.6. C$_{25}$H$_{47}$N$_2$SBr requires C, 61.6; H, 9.7; N, 5.7%).

When the above reaction is carried out in N,N-dimethylformamide as solvent and refluxing for 4 hours, the results are substantially unchanged.

EXAMPLE 20

3-Methyl-5,6,7,8-tetrahydro-thiazolo[3,2-a][1,3]diazepine (1.68 g., 0.01 mole) (prepared by basification of the hydrochloride salt with sodium carbonate in acetonitrile solution) was dissolved in dry acetonitrile and refluxed for 36 hours with cetyl bromide (3.4 g., 0.011 mole). The solvent was evaporated and the residue washed with toluene and dried. Recrystallization from a mixture of acetonitrile and dry ether gave 9-cetyl-3-methyl-5,6,7,8-tetrahydro-thiazolo[3,2-a][1,3]diazepinium bromide (3.9 g., 81%) m.p. 120°–121°. (Found: C, 60.5; H, 9.5; N, 6.2. C$_{24}$H$_{45}$N$_2$SBr requires C, 60.8; H, 9.5; N, 5.9%).

EXAMPLES 21 TO 41

The following examples were prepared by the general method of Example 20 starting with the appropriately substituted tetrahydrothiazolo [3,2-1][1,3]diazepine and the appropriate alkyl bromide. Table 3 shows the compounds prepared together with their melting points and analytical data.

TABLE 3

| Example No. | R¹ | R² | R³ | m.p. ° C. | Analysis % (Theoretical in brackets) | | |
|---|---|---|---|---|---|---|---|
| 21 | —(CH$_2$)$_{15}$CH$_3$ | H | —C$_6$H$_5$ | 93–94° | C, 65.3 | H, 8.9 | N, 5.2 |
|   |   |   |   |   | (C, 65.1 | H, 8.8 | N, 5.2) |
| 22 | —(CH$_2$)$_{17}$CH$_3$ | H | —C$_6$H$_5$ | 92–93° | C, 65.8 | H, 8.9 | N, 4.6 |
|   |   |   |   |   | (C, 66.0 | H, 9.0 | N, 5.0) |
| 23 | —(CH$_2$)$_{15}$CH$_3$ | —CH$_3$ | —C$_6$H$_5$ | 116–117° | C, 65.3 | H, 8.7 | N, 5.3 |
|   |   |   |   |   | (C, 65.6 | H, 8.9 | N, 5.1) |
| 24 | —(CH$_2$)$_{14}$CH$_3$ | H | —CH$_3$ | 116–117° | C, 60.1 | H, 9.5 | N, 5.8 |
|   |   |   |   |   | (C, 60.1 | H, 9.4 | N, 6.1) |
| 25 | —(CH$_2$)$_{17}$CH$_3$ | H | —CH$_3$ | 121° | C, 62.6 | H, 10.2 | N, 5.0 |
|   |   |   |   |   | (C, 62.3 | H, 9.8 | N, 5.6) |
| 26 | —(CH$_2$)$_{14}$CH$_3$ | H | —C$_6$H$_5$ | 79–80° | C, 63.2 | H, 8.5 | N, 5.5 |
|   |   |   |   |   | (C, 63.5 | H, 8.6 | N, 5.4) |
| 27 | —(CH$_2$)$_{12}$CH$_3$ | H | —CH$_3$ | 105° | C, 58.6 | H, 8.8 | N, 6.4 |
|   |   |   |   |   | (C, 58.5 | H, 9.1 | N, 6.5) |
| 28 | —(CH$_2$)$_{13}$CH$_3$ | H | —CH$_3$ | 115° | C, 59.1 | H, 9.3 | N, 6.3 |
|   |   |   |   |   | (C, 59.3 | H, 9.2 | N, 6.3) |
| 29 | —(CH$_2$)$_{13}$CH$_3$ | H | —C$_6$H$_5$ | 98° | C, 63.5 | H, 8.7 | N, 6.0 |
|   |   |   |   |   | (C, 63.9 | H, 8.7 | N, 5.5) |
| 30 | —(CH$_2$)$_{16}$CH$_3$ | H | —CH$_3$ | 123° | C, 61.4 | H, 9.8 | N, 5.7 |
|   |   |   |   |   | (C, 61.6 | H, 9.7 | N, 5.8) |
| 31 | —(CH$_2$)$_{12}$CH$_3$ | H | —C$_6$H$_5$ | 59–60° | C, 61.1 | H, 8.3 | N, 5.6 |
|   |   |   |   |   | (C, 61.1 | H, 8.2 | N, 5.5)* |
| 32 | —(CH$_2$)$_{16}$CH$_3$ | H | —C$_6$H$_5$ | 107° | C, 65.4 | H, 9.0 | N, 5.3 |
|   |   |   |   |   | (C, 65.5 | H, 8.9 | N, 5.1) |
| 33 | —(CH$_2$)$_{15}$CH$_3$ | H |  | 117–118° | C, 60.9 | H, 7.9 | N, 5.1 |
|   |   |   |   |   | (C, 61.2 | H, 7.9 | N, 4.9) |
| 34 | —(CH$_2$)$_{15}$CH$_3$ | —C$_6$H$_5$ | H | 92–94° | C, 65.2 | H, 8.9 | N, 5.4 |
|   |   |   |   |   | (C, 65.0 | H, 8.8 | N, 5.2) |
| 35 | —(CH$_2$)$_{15}$CH$_3$ | —(CH$_2$)$_4$— |   | 50–51° | C, 61.6 | H, 9.6 | N, 5.1 |
| 36 | —(CH$_2$)$_{15}$CH$_3$ | H | H | 86–87° | (C, 60.1 | H, 9.6 | N, 6.1) |
|   |   |   |   |   | (C, 60.1 | H, 9.4 | N, 6.1) |
| 37 | —(CH$_2$)$_{11}$CH$_3$ | H | —C$_6$H$_5$ | 54–55° | C, 61.7 | H, 8.0 | N, 5.5 |
|   |   |   |   |   | (C, 61.5 | H, 8.2 | N, 5.7)* |
| 38 | —(CH$_2$)$_{11}$CH$_3$ | H | —CH$_3$ | 110–111° | C, 57.8 | H, 8.0 | N, 7.4 |
|   |   |   |   |   | (C, 57.6 | H, 8.9 | N, 7.7) |
| 39 | —(CH$_2$)$_{15}$CH$_3$ | H |  | 75–80° | C, 63.5 | H, 8.8 | N, 4.9 |
|   |   |   |   |   | (C, 63.2 | H, 8.5 | N, 5.1) |
| 40 | —(CH$_2$)$_{15}$CH$_3$ | H | —⟨⟩—NO$_2$ | 147–152° | C, 59.7 | H, 7.8 | N, 7.3 |
|   |   |   |   |   | C, 60.0 | H, 7.9 | N, 7.2) |
| 41 | —(CH$_2$)$_{15}$CH$_3$ | H |  | 117–118° | C, 63.1 | H, 8.2 | N, 5.2 |
|   |   |   |   |   | (C, 62.9 | H, 8.3 | N, 5.1) |

*calculated for hemi-hydrate

EXAMPLE 42

2-Methyl-3-phenyl-5,6-dihydro-imidazo[2,1-b]thiazole (6.0 g., 0.027 mole) (prepared by basification of the hydrobromide salt with sodium carbonate solution and extraction into chloroform) and cetyl bromide (9.15 g., 0.03 mole) were refluxed in acetonitrile (50 ml.) for 12 hours. A crystalline solid separated on cooling which was collected and recrystallized from acetonitrile to yield 7-cetyl-2-methyl-3-phenyl-5,6-dihydro-imidazo[2,1-b]thiazolium bromide (12.2 g., 87%), m.p. 111°–113° C. (Found: C, 64.8; H, 8.6; N, 4.9. C$_{28}$H$_{45}$N$_2$SBr requires C, 64.5; H, 8.6; N, 5.4%).

EXAMPLES 43 TO 46

The following 7-substituted 2methyl-3-phenyl-5,6-dihydro-imidazo[2,1-b]thiazolium bromides were prepared in a similar manner to that described in Example 42 using 2-methyl-3-phenyl-5,6-dihydro-imidazo[2,1-b]thiazole and the appropriate alkyl bromide.

| Example No. | 7-substituent | m.p. | Analysis % (Theoretical in brackets) | | |
|---|---|---|---|---|---|
| 43 | —(CH$_2$)$_{14}$CH$_3$ | 113–6° | C, 63.9 | H, 8.6 | N, 5.4 |
|   |   |   | (C, 63.9 | H, 8.5 | N, 5.5) |
| 44 | —(CH$_2$)$_{16}$CH$_3$ | 107–9° | C, 64.9 | H, 9.0 | H, 5.2 |
|   |   |   | (C, 65.0 | H, 8.8 | N, 5.2) |
| 45 | —(CH$_2$)$_{17}$CH$_3$ | 114–6° | C, 65.4 | H, 9.3 | N, 5.2 |
|   |   |   | (C, 65.6 | H, 9.0 | N, 5.1) |
| 46 | —(CH$_2$)$_9$CH$_3$ | 78–79° | C, 59.5 | H, 7.6 | N, 6.2 |
|   |   |   | (C, 59.2 | H, 7.7 | N, 6.3)* |

*hemihydrate

EXAMPLE 47

Following the procedures of Examples 1 and 20, but employing the appropriate starting materials in case the following compounds are prepared.

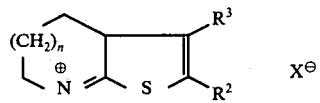

| X | R[1] | R[2] | R[3] |
|---|------|------|------|
| n = 1: | | | |
| I | $CH_3(CH_2)_{19}-$ | $4-FC_6H_4$ | $CH_3-$ |
| I | $CH_3(CH_2)_7CH(CH_3)-$ | $C_6H_5$ | $C_6H_5$ |
| Cl | $CH_3(CH_2)_9$ | $n-C_6H_{13}-$ | H |
| ½ $SO_4$ | $CH_3(CH_2)_{11}$ | $CH_3-$ | $n-C_6H_{13}-$ |
| $HSO_4$ | $CH_3(CH_2)_9$ | $(CH_3)_2CH-$ | $C_6H_5-$ |
| $C_6H_5SO_3$ | $CH_3(CH_2)_{15}-$ | $2-ClC_6H_4-$ | $CH_3-$ |
| $4-CH_3C_6H_4SO_3$ | $CH_3(CH_2)_{14}-$ | H | $2,4-Br_2C_6H_3-$ |
| Cl | 4-decyl | $4-HOC_6H_4$ | $4-HOC_6H_4$ |
| Br | $CH_3(CH_2)_{11}CH(CH_3)-$ | $3-CH_3C_6H_4-$ | H |
| Br | $CH_3(CH_2)_{13}CH(CH_3)-$ | $4-n-C_6H_{13}C_6H_4$ | |
| n = 2: | | | |
| Br | $CH_3(CH_2)_{15}$ | $4-CH_3OC_6H_4-$ | $4-CH_3OC_6H_4$ |
| ½ $SO_4$ | $CH_3(CH_2)_{15}$ | $4-n-C_6H_{13}OC_6H_4-$ | H |
| I | $CH_3(CH_2)_{19}-$ | $2-CNC_6H_4-$ | $CH_3-$ |
| $HSO_4$ | $CH_3(CH_2)_{19}-$ | $4-CF_3C_6H_4-$ | H |
| $C_6H_5SO_3$ | $CH_3(CH_2)_{14}-$ | H | $3-NO_2C_6H_4-$ |
| $4-CH_3C_6H_4SO_3$ | $CH_3(CH_2)_{15}-$ | H | $2,4-Cl_2C_6H_3-$ |
| Br | 4-decyl | $4-Br-2-CH_3OC_6H_3-$ | H |
| Br | $CH_3(CH_2)_9$ | H | $2-F-4-CH_3C_6H_3-$ |
| Cl | $CH_3(CH_2)_{19}-$ | | $-(CH_2)_4-$ |
| I | $CH_3(CH_2)_{15}-$ | H | $2-CH_3O-4-NO_2C_6H_3-$ |
| I | $CH_3(CH_2)_{15}-$ | $2,4-(CH_3)_2C_6H_3-$ | $CH_3$ |

EXAMPLE 48

Employing the procedure of Example 42 with the appropriately substituted 5,6-dihydroimidazo[2,1-b]thiazole and the appropriate compound of formula $R^1X$ in place of the starting materials used therein, the following compounds are obtained.

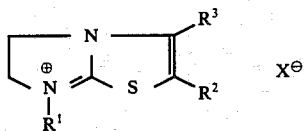

| X | R[1] | R[2] | R[3] |
|---|------|------|------|
| Cl | $CH_3(CH_2)_9-$ | $CH_3-$ | $4-FC_6H_4-$ |
| Cl | $CH_3(CH_2)_{11}-$ | $(CH_3)_2CH-$ | $C_6H_5-$ |
| I | $CH_3(CH_2)_{14}-$ | $n-C_6H_{13}-$ | $3-ClC_6H_4-$ |
| I | $CH_3(CH_2)_{15}-$ | | $-(CH_2)_4-$ |
| ½ $SO_4$ | $CH_3(CH_2)_{15}-$ | $CH_3-$ | $n-C_6H_{13}-$ |
| $HSO_4$ | $CH_3(CH_2)_{15}-$ | $CH_3CH_2-$ | $CH_3-$ |
| $HSO_4$ | $CH_3(CH_2)_9-$ | $(CH_3)_2-$ | $4-CF_3C_6H_4-$ |
| $C_6H_5SO_3$ | $CH_3(CH_2)_{11}-$ | $CH_3-$ | $3-CH_3C_6H_4-$ |
| $C_6H_5SO_3$ | $CH_3(CH_2)_{13}-$ | $CH_3-$ | $2,4-(CH_3)_2C_6H_3$ |
| $4-CH_3C_6H_4SO_3$ | 4-decyl | $CH_3-$ | $2-Br-4-HOC_6H_3-$ |
| $4-CH_3C_6H_4SO_3$ | $CH_3(CH_2)_{19}-$ | $CH_3-$ | $4-CNC_6H_4-$ |
| $2,4-(CH_3)_2C_6H_3SO_3$ | $CH_3(CH_2)_{19}-$ | $CH_3-$ | $4-CH_3O-2-NO_2C_6H_3$ |
| Br | $CH_3(CH_2)_7CH(CH_3)-$ | $CH_3CH_2-$ | $4-n-C_6H_{13}C_6H_4-$ |
| Br | $CH_3(CH_2)_{19}-$ | $CH_3-$ | $4-n-C_6H_{13}OC_6H_4-$ |
| I | $CH_3(CH_2)_{11}CH(CH_3)-$ | $CH_3-$ | $4-(CH_3)_2CHC_6H_4-$ |
| I | $CH_3(CH_2)_{15}-$ | $CH_2-$ | $4-(CH_3)_2CHOC_6H_4-$ |
| I | $CH_3(CH_2)_{15}-$ | $CH_3CH_2-$ | $2,4-Cl_2C_6H_3-$ |
| I | $CH_3(CH_2)_{16}-$ | $CH_3-$ | $2-Br-4-CH_3C_6H_3-$ |
| Cl | $CH_3(CH_2)_{13}$ | H | H |

EXAMPLE 49

Dusting Powder

An acaricidal dust is prepared as follows:

| 960 – 997.5 g. | powdered talc |
|---|---|
| 2.5 – 40 g. | 8-cetyl, 2-methyl-3-phenyl-6,7-dihydro[5H]-thiazolo[3,2-a]pyrimidinium bromide |
| 100 – 1000 ml. | Toluene |

The quaternary salt is dissolved in the toluene and the solution added to the talc such that the talc is completely wetted by the solution. The solvent is then removed by evaporation in a rotary evaporator at reduced pressure.

EXAMPLE 50

Dispersible Powder

| 25–75 g. | 9-Pentadecyl-3-phenyl-5,6,7,8-tetrahydro-thiazolo[3,2-a][1,3]diazepinium bromide |
|---|---|
| 20–73 g. | Diatomaceous earth |
| 2–5 g. | Polyethylene glycol p-isooctylphenyl ether (Igepal CA-630) |

-continued

| | |
|---|---|
| q.s. | Acetone |

The Igepal CA-630 is dissolved in acetone and added to an intimate mixture of the first two ingredients to form a thick slurry. The acetone is then removed by evaporation and the resulting mixture is milled to obtain a fine powder which may be applied to the skins of animals as a spray by dispersion in a suitable amount of water.

EXAMPLE 51

Emulsifiable Concentrate

The constituents of a suitable emulsifiable concentrate is as follows:

| Percent, w/v | |
|---|---|
| 5.0 | 7-Cetyl-2-methyl-3-phenyl-5,6-dihydro-imidazo[2,1-b]thiazolium bromide |
| 3.5 | Calcium dodecylbenzene sulphonate (Arylan CA) |
| 1.5 | Alkylphenol polyglycol ether (Ethylan BV) |
| to 100% | Mixed hydrocarbon solvent (Aramasol H) |

The emulsifying agents (Arylan CA and Ethylan BV) are dissolved in the solvent and the active ingredient then added and the mixture stirred until solution is complete. The resulting concentrate is suitably diluted with water to afford an aqueous emulsion before administration as a dip or spray to infected animals.

What is claimed is:

1. A compound of the formula:

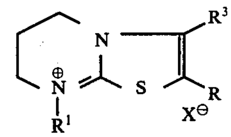

wherein $X^{\ominus}$ is a pharmaceutically acceptable anion; $R^1$ is an alkyl group having from 10 to 20 carbon atoms; when taken separately, each of $R^2$ and $R^3$ is selected from the group consisting of hydrogen, alkyl having from one to six carbon atoms, phenyl and phenyl substituted by up to two members which may be the same or different and are selected from the group consisting of fluoro, chloro, bromo, hydroxy, alkyl having from one to three carbon atoms, alkoxy having from one to three carbon atoms, cyano, nitro and trifluoromethyl, and when $R^2$ and $R^3$ are taken together they form a tetramethylene group.

2. A compound according to claim 1 wherein $R^1$ is alkyl having from 10 to 18 carbon atoms and $X^{\ominus}$ is chloride, bromide or iodide ion.

3. A compound according to claim 2 wherein $X^{\ominus}$ is bromide ion.

4. A compound according to claim 3 wherein $R^2$ is hydrogen or methyl and $R^3$ is methyl, ethyl or phenyl.

5. The compound according to claim 4 wherein $R^1$ is n-tetradecyl, $R^2$ is methyl and $R^3$ is ethyl.

6. The compound according to claim 4 wherein $R^1$ is n-hexadecyl, $R^2$ is methyl and $R^3$ is ethyl.

7. The compound according to claim 4 wherein $R^1$ is n-hexadecyl, $R^2$ is methyl and $R^3$ is phenyl.

8. A compound according to claim 4 wherein $R^1$ is n-pentadecyl n-hexadecyl, or n-heptadecyl, $R^2$ is hydrogen and $R^3$ is phenyl.

* * * * *